(12) United States Patent
Hensley et al.

(10) Patent No.: US 6,346,544 B2
(45) Date of Patent: Feb. 12, 2002

(54) DESMETHYL TOCOPHEROLS FOR PROTECTING CARDIOVASCULAR TISSUE

(75) Inventors: Kenneth L. Hensley; Robert A. Floyd, both of Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/794,292

(22) Filed: Feb. 27, 2001

Related U.S. Application Data

(60) Provisional application No. 60/186,455, filed on Mar. 2, 2000.

(51) Int. Cl.$^7$ ............................................. A61K 31/355
(52) U.S. Cl. ...................................................... 514/458
(58) Field of Search ......................................... 514/458

(56) References Cited

U.S. PATENT DOCUMENTS

| | | | |
|---|---|---|---|
| 5,908,940 A | * | 6/1999 | Lane et al. .................. 549/413 |
| 6,045,826 A | * | 4/2000 | Borowy-Borowski et al. ... 424/451 |
| 6,048,891 A | * | 4/2000 | Wechter ...................... 514/456 |

OTHER PUBLICATIONS

Bieri, J. G., Evarts, R. P. Gamma tocopherol: Metabolism, biological activity and significance in human vitamin E nutrition. *J. Clin. Nutr.* 27:980–985; 1974.

Lehmann, J.; Martin, H. L.; Lashley, E. L.; Marshall, M. W.; Judd, J. T. Vitamin E in foods from high and low linoleic acid diets. *J. Am. Diet. Assoc.* 86, 1206–1216; 1986.

Handelman, G. J.; Machlin, L. M.; Fitch, K.; Weiter, J. J.; Dratz, E. A. Oral α–tocopherol supplements decrease plasma γ–tocopherol levels in humans. *J. Nutr.* 115: 807–813; 1985.

Traber, M. G.; Burton, G. W.; Hughes, L.; Ingold, K. U.; Hidaka, H.; Malloy, M.; Kane, J.; Hyams, J.; Kayden, H. J. Discrimination between forms of vitamin E by humans with and without genetic abnormalities of lipoprotein metabolism. *J. Lipid Res.* 33, 1171–1182; 1992.

Cooney, R. V.; Franke, A. A; Harwood, P. J.; Hatch–Pigott, V.; Custer, L. J.; Mordan, L. J. γ–Tocopherol detoxification of nitrogen dioxide: Superiority to α–tocopherol. *Proc. Natl. Acad. Sci. USA*. 90:1771–1775, 1993.

Christen, S.; Woodall, A. A.; Shigenaga, M. K.; Southwell–Keely, P. T.; Duncan, M. W.; Ames, B. N. γ–Tocopherol traps mutagenic electrophiles such as NOx and complements α–tocopherol: Physiological implications. *Proc. Natl. Acad. Sci. USA* 94:3217–3222; 1997.

Goss, S. P. A.; Hogg, N.; Kalyanaraman, B. The effect of α–tocopherol on the nitration of γ–tocopherol by peroxynitrite. *Arch. Biochem. Biophys.* 363: 333–340; 1999.

Dillard, C. J.; Gavino, V. C.; Tappel, A. L. Relative antioxidant effectiveness of α–tocopherol and γ–tocopherol in iron–loaded rats. *J. Nutr.* 113:2266–2273; 1983.

Saldeen, T.; Li, D.; Mehta, J. L. Differential effects of alpha–and gamma–tocopherol on low–density lipoprotein oxidation, superoxide activity, platelet aggregation and arterial thrombogenesis. *J. Am. Coll. Cardiol.* 34:1208–1215; 1999.

Tran, K.; Chan, A. C. Comparative uptake of alpha–and gamma–tocopherol by human endothelial cells. *Lipids* 27:38–41; 1992.

Brown, M. S.; Goldstein, J. L. A receptor–mediated pathway for cholesterol homeostasis. *Science* 232:34–37; 1986.

Goldstein, J. L.; How, Y. K.; Basu, S. K.; Brown, MS. Binding site on macrophages that mediates uptake and degradation of acetylated low density lipoprotein, producing massive cholesterol deposition. *Proc. Natl. Acad. Sci. USA* 76:333–337, 1979.

Palinski, W.; Rosenfeld, M. E.; Yla–Herttuala, S. Gurtner, G. C.; Socher, S. S.; Butler, S. W.; Parthasarathy, S.; Carew, T. E.; Steinberg, D.; Witztum, J. L. Low density lipoprotein undergoes oxidative modification in vivo. *Proc. Natl. Acad. Sci. USA* 86:1372–1376; 1989.

Quinn, M. T.; Parasarathy, S.; Fong, L. G.; Steinberg, D. Oxidatively modified low density lipoproteins: A potential role in recruitment and retention of monocyte/ macrophage during atherogenesis. *Proc. Natl. Acad. Sci. USA* 84:2995–2998; 1987.

Witztum, J. ; Steinberg, D. Role of low density lipoprotein in atherogenesis. *J. Clin. Invest.* 88: 1785–1792; 1991.

Esterbauer, H.; Gebicki, J.; Puhl, H.; Jurgens, G. The role of lipid peroxidation and antioxidants in modification of LDL. *Free Rad. Biol. Med.* 13:341–390; 1992.

Steinbrecher, U. P.; Lougheed, M. Scavenger receptor–independent stimulation of cholesterol esterification in macrophages by low density lipoprotein extracted from human aortic intima. *Arterioscler. Thromb.* 12:608–625; 1992.

Jessup, W.; Rankin, S. M. De Whalley, C. V.; Hoult, J. R. S.; Scott, J.; Leake, D. S. α–Tocopherol consumption during low–density lipoprotein oxidation. *Biochem. J.* 265:399–405; 1990.

Suarna, C.; Dean, R. T.; May, J.; Stocker, R. Human artherosclerotic plaque contains both oxidized lipids and relatively large amounts of alpha tocopherol and ascorbate. *Arterioscler. Thromb. Vasc. Biol.* 15: 1616–1624; 1995.

(List continued on next page.)

*Primary Examiner*—Raymond Henley, III
(74) *Attorney, Agent, or Firm*—Head, Johnson & Kachigian

(57) ABSTRACT

The present invention involves the use of desmethyl tocopherols such as gamma tocopherol for the protection of cardiovascular tissue from nitrative stress. While mechanisms other than scavenging of reactive nitrogen species may be involved, desmethyl tocopherols exhibit significant protection and may be utilized to treat or help prevent cardiovascular particularly arterial vascular disease. The desmethyl tocopherols may be administered dietarily or parenterally when a more direct dosage is desired. Both routes may be utilized together or separately to optimize therapeutic and prophylactic benefits. The lessening of damage induced by reactive nitrogen species leads to the lessening of arterial blockage in thrombosis.

16 Claims, 3 Drawing Sheets

OTHER PUBLICATIONS

Diaz, M. N.; Frei, B. Vita, J. A.; Keaney, J. F. Jr. Antioxidants and atherosclerotic heart disease. *New Eng. J. Med.* 337:408–416; 1997.

Baker, C. S.; Hall, R. J.; Evans, T. J.; Pomerance, A.; Maclouf, J.; Creminon, C.; Yacoub, M. H.; Polak, J. M. Cyclooxygenase–2 is widely expressed in atherosclerotic lesions affecting native and transplanted human arteries and colocalizes with inducible nitric oxide synthase and nitrotyrosine particularly in macrophages. *Arterioscler. Thromb. Vasc. Biol.* 19:646–655; 1999.

Luoma, J. S.; Stralin, P.; Marklund, S. L.; Hiltunen, T. P.; Sarkioja, T.; Yla–Herttuala, S. Expression of extracellular SOD and iNOS in macrophages and smooth muscle cells in human and rabbit atherosclerotic lesions: Colocalization with epitopes characteristic of oxidized LDL and peroxynitrite–modified proteins. *Arterioscler. Thromb. Vasc. Biol.* 18:157–167; 1998.

Buttery, L. D.; Springall, D. R.; Chester, A. H.; Evans, T. J.; Standfield, E. N.; Parums, D. V.; Yacoub, M. H.; Polak, J. M. Inducible nitric oxide synthase is present within human atherosclerotic lesions and promotes the formation and activity of peroxynitrite. *Lab Invest.* 75:77–85, 1996.

Luoma, J. S.; Yla–Herttuala, S. Expression of inducible nitric oxide synthase in macrophages and smooth muscle cells in various types of human atherosclerotic lesions. *Virchows Arch* 434:561–568; 1999.

Behr, D.; Rupin, A.; Fabiani, J. N.; Verbeuren, T. J. Distribution and prevalence of inducible nitric oxide synthase in atherosclerotic vessels of long–term cholesterol–fed rabbits. *Atherosclerosis* 142:335–344; 1999.

Leeuwenburgh, C.; Hardy, M. M.; Hazen, S. L.; Wagner, P.; Oh–ish, S.; Steinbrecher, U. P.; Heinecke, J. W. Reactive nitrogen intermediates promote low–density lipoprotein oxidation in human atherosclerotic intima. *J. Biol. Chem.* 17:1433–1436; 1997.

Moriel, P.; Abdalla, D. S. Nitrotyrosine bound to beta–V-LDL apoproteins: A biomarker of peroxynitrite formation in experimental atherosclerosis. *Biochem. Biophys. Res. Commun.* 232:332–335; 1997.

Spencer, A. P.; Carson, D. S.; Crouch, M. A. *Arch. Intern. Med.* 159: 1313–1320; 1999.

Gey, K. F.; Puska, P.; Moser, U. K. Inverse correlation between plasma vitamin E and mortality from ischemic heart disease in cross–cultural epidemiology. *Am. J. Clin. Nutr.* 53 (suppl. 1): 326S–334S; 1991.

Stampfer, M. J.; Hennekens, C. H.; Manson, J. E.; Coldizt, G. A.; Rosner, B.; Willett, W. C. Vitamin E consumption and the risk of coronary heart disease in women. *N. Engl. J. Med.* 328;1444–1449; 1993.

Rimm, E. B.; Stamfer, M. J.; Ascherio, A.; Giovannucci, E.; Colditz, G. A.; Willett, W. C. Vitamin E consumption and the risk of coronary heart disease in men. *N. Engl. J. Med.* 328:1450–1456; 1993.

Stephens, N. G.; Parsons, A.; Schofield, P. M.; Kelly, F.; Cheeseman, K.; Mitchinson, M. J. Randomised controlled trial of vitamin E in patients with coronary disease: Cambridge Heart Antioxidant Study (CHAOS) *Lancet* 347: 781–786; 1996.

Rapola, J. M.; Virtamo, J.; Ripatti, S.; Huttumen, J. K.; Albanes, D.; Taylor, P. R.; Heinonen O. P. Randomised trial of alpha tocopherol and beta carotene supplements on incidence of major coronary events in men with previous myocardial infarction. *Lancet* 349:1715–1720; 1997.

Subcommittee on the Tenth Edition of the RDAs, Food and Nutrition board, Comission on Life Sciences, National Research Council. Recommended Dietary Allowances. $10^{th}$ed. Washington, DC: National Academy Press; 1989.

The alpha–tocopherol beta carotene cancer prevention study group. The effect of vitamin E an beta carotene on the incidence of long cancer and other cancers in male smokers. *New Engl. J. Med.* 330:1029–1035; 1994.

Kushi, L. H.; Folsom, A. R.; Prineas, R. J.; Mink, P. J.; Wu, Y.; Bostick, R. M. Dietary antioxidant vitamins and death from coronary heart disease in postmenopausal women. *N. Engl. J. Med.* 328: 1156–1162; 1996.

Stocker, R. The ambivalence of vitamin E in atherogenesis. *Trends Biol. Sci.* 24:219–223; 1999.

The heart outcomes prevention evaluation study investigators. Vitamin E supplementation and cardiovascular events in high–risk patients. *New Engl. J. Med.* 342:154–160; 2000.

Kontush, A.; Spranger, T.; Reich, A.; Baum, K.; Beisiegel, U. Lipophilic antioxidants in blood plasma as markers of atherosclerosis: The role of α–carotene and γ–tocopherol. *Atherosclerosis* 144: 117–122; 1999.

Ohrvall, M.; Sundlof, G.; Vessby, B. Gamma, but not alpha, tocopherol levels in serum are reduced in coronary heart disease patients. *J. Int. Med.* 239: 111–117; 1996.

Brown, A. J. Acute effects of smoking cessation on antioxidant status. *J. Nutr. Biochem.* 7:29–39; 1996.

Cooney, G. J.; Taegtmeyer, H.; Newsholme, E. A. Tricarboxylic acid cycle flux and enzyme activities in the isolated working rat heart. *Biochem. J.* 200: 701–703; 1981.

Lucas, D. T.; Szweda, L. I. Declines in mitochondrial respiration during cardiac reperfusion: Age–dependent inactivation of alpha ketoglutarate dehydrogenase. *Proc. Natl. Acad. Sci. USA* 96:6689–6693. (1983).

Brown, J. P.; Perham, R. N. Selective inactivation of the transacylase components of the 2–oxoacid dehydrogenase multienzyme complexes of *Escherichia coli. Biochem. J.* 155: 419–427; 1976.

Andersson, U.; Leighton, B.; Young, M. E.; Blomstrand, E.; Newsholme, E. A. Inactivation of aconitase and oxoglutarate dehydrogenase in skeletal muscle in vitro by superoxide anions and/or nitric oxide. *Biochem. Biophys. Res. Commun.* 249:512–516. (1991).

Park, L. C.; Zhang, H.; Sheu, K. F.; Calingasan, N. Y.; Kristal, B. S.; Lindsay, J. G.; Gibson, G. E. Metabolic impairment induces oxidative stress, compromises inflammatory responses, and inactivates a key mitochondrial enzyme in microglia. *J. Neurochem.* 72: 1948–1958; 1999.

Kjellman, U.; Bjork, K.; Ekroth, R.; Karlsson, H.; Jagenburg, R.; Nilsson, F.; Svensson, G.; Wernerman, J. Alpha-–ketoglutarate for myocardial protection in heart surgery. *Ann. Thor. Surg.* 63: (1997).

Kjellman, U. W.; Bjork, K.; Ekroth, R.; Karlsson, H.; Jagenburg, R.; Nilsson, F. N.; Svensson, G.; Wernerman, J. Addition of alpha–ketoglutarate to blood cardioplegia improves cardioprotection. *Ann. Thorac. Surg.* 63:1625–1633; 1997.

Freedman, J. E.; Farhat, J. H.; Loscalzo, J.; Keaney, J. F. Jr. α–Tocopherol inhibits aggregation of human platelets by a protein kinase C–dependent mechanism. *Circulation* 94: 2434–2440; 1996.

Keaney, J. F. Jr.; Simon, D. I.; Freedman, J. Vitamin E and vascular homeostasis: Implications for atherosclerosis. FASEB J. 13:965–976; 1999.

Pignatelli, P.; Pulceinelli, F. M.; Lenti, L.; Gazzaniga, P. P.; Violi, F. Hydrogen peroxide is involved in collagen–induced platelet activation. *Blood* 91: 484–490; 1998.

Pignatell, P.; Pulcinelli, F. M.; Leni, L.; Gazzaniga, P. P.; Violi, F. Vitamin E inhibits collagen–induced platelet activation by blunting hydrogen peroxide. *Arterioscler. Thromb. Vasc. Biol.* 19:2542–2547; 1999.

* cited by examiner

DESMETHYL TOCOPHEROLS FOR PROTECTING CARDIOVASCULAR TISSUE

CROSS-REFERENCE TO RELATED APPLICATIONS

Priority is claimed from provisional application U.S. Ser. No. 60/186,455 filed on Mar. 2, 2000, and incorporated by reference herein.

BACKGROUND

The present invention relates to concentrated preparations of desmethyl tocopherols, including but not restricted to gamma tocopherol (γT), which localize to lipid environments in cardiovascular tissue and scavenge reactive nitrogen species (RNS) by virtue of a phenolic structural element lacking one or more methyl substituents on the phenolic ring system. The capability to scavenge RNS imparts cardiovascular protective properties to the compound.

Tocopherols are a class of lipophilic, phenolic compounds of plant origin. The major tocopherol found in mammalian tissue is alpha tocopherol (α-tocopherol or αT or vitamin E) FIG. 1, although significant quantities of demethylated (desmethyl) forms (particularly γ-tocopherol or γT) FIG. 1, are also present. α-Tocopherol acts as a free radical scavenger (i.e., a chain-breaking antioxidant) when the phenolic head group encounters a free radical:

Toc-OH+L.→Toc-O.+LH  Toc-OH=tocopherol L.=lipid radical

The phenoxyl radical Toc-O. is much more stable, and less reactive, than L.. The aromatic nature of the tocopherol ring system, combined with steric and electronic influences from the methyl The phenoxyl radical Toc-O. is much more stable, and less reactive, than L.. The aromatic nature of the tocopherol ring system, combined with steric and electronic influences from the methyl substituents, stabilizes the tocopheroxyl radical and thereby ends the lipid peroxidation process. Eventually, Toc-O. is reduced back to Toc-OH by ascorbate acting in conjunction with NADPH reductase. While α-tocopherol is the major tocopherol in the body, other tocopherols exist. The second major tocopherol in the human body is γ-tocopherol (γT), which, like α-tocopherol, is made by plants and taken into the human diet with foodstuffs.

Recently, it has become appreciated that reactive nitrogen species (RNS) are significant to many diseases including coronary artery disease (CAD), hypertension, and other forms of cardiovascular disease where localized inflammatory reactions occur. RNS are derived from the enzymatic oxidation of arginine via the intermediate nitric oxide free radical (FIG. 2). Unlike oxygen-centered free radicals, reactive nitrogen species are not scavenged effectively by α-tocopherol. On the other hand, γ-tocopherol can react easily with RNS because of the presence of an open space on the chromanol head of the molecule (FIG. 1). The major product of γ-tocopherol reaction with RNS is 5-nitro-γ-tocopherol (5NγT, FIG. 1). Recent discoveries indicate that: (A) γT protects biological systems from RNS much more effectively than αT; (B) γT is extensively nitrated in human plasma, particularly among smokers and hypertensive individuals; (C) γT inhibits RNS toxicity to a critical enzyme (α-ketoglutarate dehydrogenase, or αKGDH) which is severely damaged in injured vascular tissue; and (D) γT protects cultured endothelial cells from RNS. Thus, γT possesses unique biochemical functions from αT that suggest γT may be a superior dietary supplement, cardioprotectant, cardioplegia additive, or a preservative in cardiovascular tissue exposed to RNS. Other desmethyl tocopherols likewise should be cardioprotective by this mechanism or another.

Chemistry of tocopherol reaction with oxidizing agents. γ-Tocopherol is a natural product (a desmethyl tocopherol) of plant origin, present in many vegetable oils, especially soybean oil (1–2). γ-Tocopherol is normally taken into the body through consumption of foodstuffs. Human plasma γT concentration is variously reported as 5–30% of αT (3). The γT⁄αT ratio varies markedly among individuals; plasma γT/αT proportionalities may be as low as 0.2% and as high as 30% (inventors' observations). Both αT and γT are absorbed equally well by the gut, but γT is packaged into lipoproteins less effectively than αT (4). For this reason, αT supplementation decreases systemic γT concentration (3–4).

To date, only three well-disseminated studies have compared αT and γT with respect to their ability to inhibit nitrative stress specifically (5–7). These studies generally investigated the in vitro reaction of nitrating equivalents with target substrates in "pure" chemical systems, and two of the three studies reached very different conclusions. The first investigation from Cooney's lab (5) reported that γT reaction with NO$_2$ gas was 6 times more rapid than the corresponding reaction of αT. Furthermore, exposure of αT (but not γT) to NO$_2$ caused the formation of a secondary nitrating species which could nitrate the target compound morpholine (5). In the same manuscript, Cooney et al. showed that γT was 4-fold more effective than αT at inhibiting neoplastic transformation of methylcholanthrene-treated C3H/10T1/2 fibroblasts, a process which the authors suggest might involve nitrative stress (5). The second study (Christen et al. 1997; reference 6) incorporated either αT or γT, or both, into liposomes which were then exposed to synthetic peroxynitrite (ONOO⁻). Christen and colleagues found that γT was twice as effective as αT at inhibiting lipid hydroperoxide formation in liposomes exposed to ONOO⁻. Moreover, these researchers found that γT nitration rates were not influenced by the presence of αT. This latter finding suggests that nitration of γT may occur preferentially to reaction with αT when both tocopherols are simultaneously exposed to a nitrating species. In the third study (7), Goss et al. take issue with the findings of Christen et al. and report that αT does spare γT in liposomes exposed to the superoxide and NO-generating compound SIN-1 [5-amino-2-(4-morpholinyl)-1,2,3-oxadiazolium].

A search of the literature revealed only two studies in which αT and γT were compared for efficacy using in vivo models of cardiovascular stress (no studies were found investigating neurological stress). In the first study (c. 1983), tocopherol-depleted rats were fed αT or γT for two weeks after chronic exposure to iron-dextran as an inducer of oxyradical stress (8). While both αT and γT inhibited systemic lipid oxidation in the animals, γT was approximately 35% as effective as αT. Lipid nitration was not an endpoint of this investigation, and physiologic parameters were not recorded. In a second, very recent study (reference 9; Saldeen et al., *J. Am. Coll. Card.*, Oct. 1999), rats on an otherwise normal diet were fed αT or γT (100 mg/kg/day) for 10 days after which the abdominal aorta was exposed to patch soaked in 29% FeCl$_3$ (9). This stress induced obstructive thrombus within 20 minutes. Saldeen et al. found that γT supplementation was significantly more effective than αT supplementation at inhibiting iron-induced lipid peroxidation and occlusive thrombus (9). Time to occlusive thrombus was delayed by 25% in the αT supplemented animals while the same parameter was increased by 65% in γT supplemented animals (9). Platelet aggregation kinetics were similarly inhibited, with γT supplementation being 2-fold more efficacious than αT supplementation (9). Most importantly, the γT concentration in the plasma of the γT supplemented rats never exceeded 10% of the αT concentration although the feeding paradigm did increase γT levels 6-fold above baseline (9). By comparison, αT supplementation increased αT plasma concentration only 2-fold (9). When treatment effects were considered in reference to plasma tocopherol concentrations, the Saldeen study found γT to be 20–30 times more potent than αT at inhibition of throbogenic correlates. No conclusive explanation for the γT effect was offered by the Saldeen study, though superoxide dismutase activity increased significantly in the aortas of γT treated animals as compared to the αT treated group (9). The unexpected efficacy of γT might also stem from a differential vascular partitioning of γT, since γT is reportedly incorporated into endothelial cells more rapidly than is αT (10). In any case, the efficacy of γT as a vascular or neuroprotectant cannot be predicted from its bioactivity in traditional fertility assays, or from its oxyradical scavenging capacity as measured in vitro.

Role of oxidative and nitrative stress in atherosclerosis. Oxidative stress is centrally involved with both the initiation and the progression of atherosclerosis. In normal vasculature, low density lipoprotein (LDL) crosses the endothelium to provide lipids and cholesterol to the vascular intima. Normal LDL is taken up in by specific cell-surface receptors whose expression is tightly regulated so as to preclude intracellular accumulation of cholesterol. Chemically-modified LDL, including oxidized LDL (oxLDL), is taken up more rapidly and less specifically, particularly by macrophages (11–22). The accumulation of excessive oxLDL converts these into "foam cells", a hallmark of early atherosclerosis (12). Oxidized lipids and proteins are abundant in atherosclerotic lesions, though the specific nature of the oxidative modifications is unclear (13–16). LDL can be oxidized in vitro by exposure to metal-catalyzed oxyradical generating systems, and this oxLDL will convert macrophages into foam cells (13,16); however, this "synthetic" oxLDL differs from natural oxLDL in several respects. Synthetic oxLDL is taken up by macrophage scavenger receptors only after complete depletion of αT resident within the LDL particle (18). Natural oxLDL is not recognized by the scavenger receptor, indicating that the chemical modification of natural oxLDL is different from that of in vitro modified LDL (17). Moreover, αT content of native oxLDL is not substantially depleted, even in extracts taken from severe lesions (19). OxLDL is chemotactic and stimulates expression of vascular adhesion molecules, thereby recruiting leukocytes to the subendothelial space (14). Neutrophils and macrophages may become activated in this milieu, releasing pro-inflammatory cytokines and generating more ROS and reactive nitrogen species. Chronic exposure to oxLDL causes macrophage and endothelial death and release of lipids from the dying cells (reviewed in 20). Further leukocyte recruitment to the necrotic focus accelerates the atherogenic process. An additional consequence of subendothelial inflammation is proliferation of VSM cells in response to cytokine exposure, which further decreases perfusion through the affected vessel (20). End-stage disease is characterized by ischemic damage to the heart and major perfused organs, and with increased risk of occlusive thrombus as portions of plaque disintegrate and initiate coagulation cascades.

As previously discussed, the combination of NO with superoxide or other leukocyte-derived oxidants yields peroxynitrite and other nitrating agents. Furthermore, activated macrophages produce profligate quantities of NO via iNOS (inducible nitric oxide synthate). It therefore appears that NO-derived products play a role in vascular modification during atherosclerosis. iNOS and nitrotyrosine have been immunochemically detected in human atherosclerotic plaques, where most staining occurs in foam cells and VSM cells (21–24). Some iNOS is present in VSM even in normal vessel walls (24). Similar iNOS immunoreactivity is found in experimental atheroscerotic lesions of hypercholesterolemic rabbits (25). Endothelial cells express very little iNOS in vivo or in vitro; however, the endothelium is likely to encounter nitrating agents derived from other cell types. Combination of eNOS (endogenous nitric oxide synthate)-derived NO with leukocyte-derived ROS might also form peroxynitrite in the subendothelial space. Quantitative mass spectrometric studies indicate that LDL isolated from human atherosclerotic plaques contains 100 times more nitrotyrosine than LDL from normal plasma (26). Similar LDL protein nitration is observed in rabbits fed a high cholesterol diet (27). Lipid nitration in atherosclerosis has not been investigated.

α-Tocopherol in human cardiovascular disease. Considering the importance of lipoprotein oxidation in the pathogenesis of atherosclerosis, it seems logical that α-tocopherol should decrease the incidence or severity of CAD. In the period from 1985–1995, numerous epidemiological, cross-sectional and observational studies were undertaken to determine if this might be the case. Initial studies using relatively small populations (<100 subjects) failed to find a correlation between α-T and vascular disease, although these studies have been criticized for failure to normalize αT to lipid content, which might confound the interpretation of the data (28). A 1991 study by Gey et al. correlated ischemic heart disease (IHD) rates with lipid-standardized αT concentrations using mean values obtained from male populations in 16 European nations (29). A highly significant negative correlation (®=0.79) was found between these parameters, indicating a beneficial role for αT in IHD. The authors conclude that a 40% increase in plasma αT was associated with an 84% lower mortality rate.

Data from cross-sectional and epidemiological human studies generally support the contention that αT is protective against vascular pathology, though perhaps not in all human populations. In the hope of overcoming limitations inherent to cross-sectional studies, several large-scale, longitudinal investigations were undertaken in the early 1990s to formally test the importance of α-T as a vasoprotectant. The "US Nurses' Health Study" analyzed self-reported vitamin E intake among 87,425 American nurses over 8 years (30) and found a 34% diminished risk of coronary disease among subjects within the upper quintile of αT consumption compared to subjects within the lowest quintile. In a similar study (the Health Professions Follow-up Study) involving 39,910 men, the risk of CAD was diminished by 39% for men with a median tocopherol intake of 419 vs. 6.4 IU/day (1 IU=1 mg d-α-tocopherol acetate; 31). From these studies, a daily intake of 100 IU of αT is most consistently associated with benefit (28) while the US Reference Daily Intake for vitamin E is 15 IU/day (34). These several investigations did not discriminate thoroughly between "dietary" versus "supplementary" sources of αT, and no specific consideration was made of γT or other co-antioxidants. In the one large study which has attempted to discriminate between dietary vitamin E and vitamin supplements, 35,000 post-menopausal women were followed for 7 years (the "Women's Health Study", ref. 36). Cardiovascular death was negatively associated with high intake of vitamin E from food, while no benefit was apparent when vitamin E supplements were evaluated alone or in combination with dietary vitamin E intake (36).

Data from large-scale, prospective, controlled tocopherol supplementation trials is currently being analyzed and published with somewhat paradoxical results. Despite epidemiological evidence that α-T correlates inversely with vascular disease, controlled αT supplementation has a relatively subtle protective effect against CAD and possibly a detrimental effect on hemorrhagic pathology. In the Cambridge Heart Antioxidant Study (CHAOS), 2002 male smokers with angiographically proved CAD received vitamin E supplements of 400–800 IU/day and were followed for 18 months (32). In this study, vitamin E supplements caused a significant 77% reduction in nonfatal myocardial infarction but a 29% increase in all-cause mortality. In a similar study involving 1,862 male smokers with previous myocardial infarction, a 50 mg/kg supplement of vitamin E had no effect on MI or mortality after 5.3 years of follow-up (33). An independent study reports that 50 IU/day of αT does not decrease total mortality of smokers but increases death from hemorrhagic stroke after 5–8 years (35). Interestingly, plasma αT increased 50% in this latter supplementation paradigm, a quantity previously associated with an 80% reduction of ischemic heart disease in the cross-cultural epidemiological study by Gey et al. (29). In the most recent evaluation of αT, the Heart Outcomes Prevention Evaluation (HOPE), Canadians at risk for heart disease were studied (38). In a total population of 9541 subjects, 400 IU/day of "natural" αT had no effect on primary or secondary cardiovascular outcomes or death over a 4.5 year period (38). The quantitative discrepancies between epidemiological data and intervention studies are disturbing. The disparity may indicate that αT can inhibit the development of CAD in the early stages but not in more advanced clinical conditions. Alternatively, it has been suggested that intake of αT from food is correlated with the intake of other co-antioxidants which are required for maximal cardiovascular benefit, and that current αT supplementation paradigms fail to take into account these necessary "cofactors" (36–37). The identity (identities) of these putative "cofactors" has not been suggested.

γ-Tocopherol in human biology and cardiovascular disease. Relative to αT, a dearth of epidemiological data exists for γT. Human plasma γT concentration is variously reported as between 5–30% that of αT (41). In platelet-poor plasma, we find that 7% is very close to the correct value in young healthy subjects. The γT/αT ratio varies markedly among individuals; we have observed plasma γT/αT proportionalities as low as 0.2% and as high as 30%. γT is now a major tocopherol in the US diet, due to the high intake of soybean and vegetable oils that are abundant sources of γT (40). Both αT and γT are absorbed equally well by the gut, but γT is packaged into lipoproteins less effectively than αT (39). For this reason, αT supplementation decreases systemic γT concentration (41–42). δ-Tocopherol, β-tocopherol and tocol (other demethylated tocopherol homologs) exist in human plasma at approximately 1:10 ratios relative to γT (41). Detailed demographic data regarding plasma and tissue levels of desmethylated tocopherols and their oxidation products have never been published. While extensive data has been collected on α-tocopherol as a possibly beneficial molecule in cardiovascular disease, very little data has been collected on γT.

The small amount of published clinical data regarding γ-tocopherol is provocative. Two small studies have investigated γT in CAD. A 1999 study reports a 40% decrease in plasma γT in patients (N=34) with atherosclerosis while αT increased by 30% (43). An earlier 1996 study by Ohrvall et al. found that CAD patients (N=69) had a significant 25% reduction in lipid-normalized plasma γT concentration while αT was statistically unaffected (44). In the latter study, the ratio of γT/αT in the CAD patients was decreased by 35% (44). Importantly, Ohrvall et al. note that very few of the CAD patients had supplemented their diet with vitamin E preparations. Tocopherol oxidation and nitration products were not measured in either study. In a separate but very remarkable study of smokers (a group at high risk for vascular disease), plasma γT levels were reduced by more than 50% in chronic smokers while plasma αT concentration was diminished by only 20–25% (45). Moreover, cessation of smoking for 84 hours resulted in a 35% recovery of γT in plasma and a 65% recovery of γT in low density lipoprotein (LDL) while αT recovery was not significant. Interestingly, the magnitude of γT rebound following cessation of tobacco use correlated very strongly with the extent of tobacco use preceding the period of voluntary abstinence (45). Again, tocopherol oxidation and nitration products were not measured. While several high-profile studies have shown αT intake somewhat protective against CAD in smokers (45), no similar studies have been undertaken using γT as an independent variable.

While chronic αT supplementation can increase plasma levels of αT by 300–400%, very little data exists regarding the effect of dietary γT. To the knowledge of the P.I., no serious attempt has been made to increase plasma γT in humans in the context of a formal scientific study. Several small studies using very small study populations have indicated that dietary supplementation with αT decreases plasma γT in humans and rodents (41–42), while chronic dietary supplementation of γT might conceivably increase plasma and tissue γT concentration. The human biology of other, less common desmethylated tocopherols is essentially uninvestigated. It cannot be assumed, however, that the relative importance of the various tocopherols can be anticipated solely on the basis of their relative tissue concentrations, independent of other biochemical variables.

The present invention is intended to solve the problems described above, namely, the inefficacy of α-tocopherol (vitamin E) to adequately protect against cardiovascular disease in clinical investigations, and to improve the ability of the tocopherol to inhibit the progression of cardiovascular diseases including but not limited to atherosclerosis. The mechanism of the invention at least in part involves the improved ability of a tocopherol desmethyl homolog to scavenge reactive nitrogen species (RNS).

SUMMARY OF INVENTION

The present invention involves the use of γ-tocopherol and other desmethyl tocopherols as scavengers of reactive nitrogen or other reactive species in tissue exposed to an inflammatory stress, particularly in cardiovascular tissue exposed to nitrative stress. The preferred desmethyl tocopherols of the present invention have the following structures:

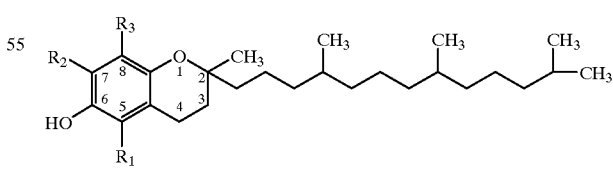

The only constraint placed on the structure above is that at least one of the set $R_1$, $R_2$ and $R_3$ must be a H atom. Additionally, the alkyl (linear, branched, or cyclic) tail of the molecule may include either saturated or unsaturated variants (unsaturated variants comprising the chemical subclass of tocotrienol tocopherols). Since the main bioactive function of the above structure is the phenolic head group, any stereoisomer of the tocopherol may be used. Furthermore, since the main bioactive function of the above structure is the phenolic head group, any carbon can be eliminated from the carbon centers labeled 2–4 in the structure above. Furthermore, the —OH group can be esterified or otherwise modified to form a prodrug or a more water-soluble derivative such as an ester, for example, which would regenerate the —OH group in vivo.

These and other homologs of the tocopherols can be chemically synthesized or isolated from natural products. In the method of the present invention, the tocopherols are administered in a safe and effective amount to scavenge reactive nitrogen or other species and slow the progression of nitrative stress in tissue undergoing progressive degeneration. These and other advantages and objects of the invention will be apparent to those skilled in the art.

The present invention also involves a method for protecting or delaying cardiovascular disease, its symptoms, consequences, or related damage. Cardiovascular disease includes ischemia disease (including thrombosis). Mitochondrial function of the myocardial is likewise protected.

DETAILED DESCRIPTION OF THE INVENTION

Figure 1:
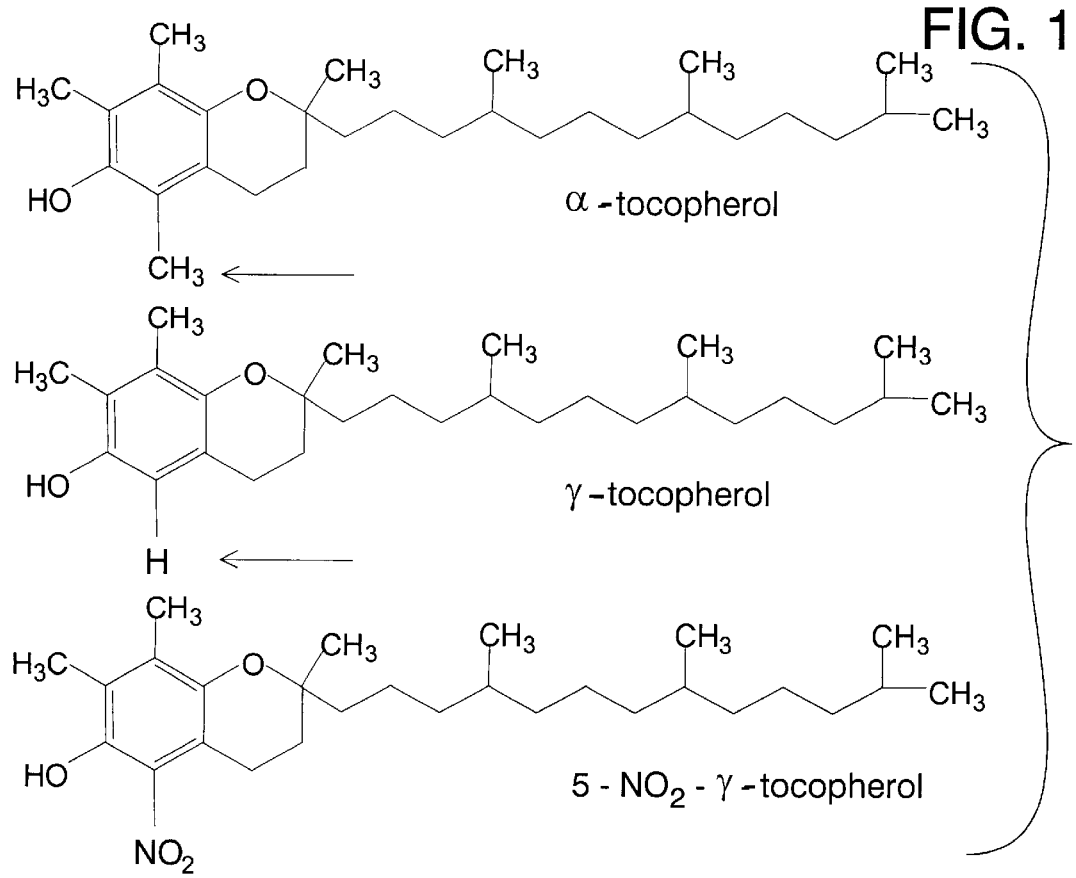
FIG. 1 shows tocopherol structures. Arrows indicate the 5 position of the chromanol ring system, which is methylated in α-tocopherol (vitamin E) but not in γ-tocopherol. This structure difference allows γ-tocopherol to scavenge RNS in a manner that α-tocopherol cannot. The product of the scavenging reaction is 5-nitro-γ-tocopherol.
Figure 2:
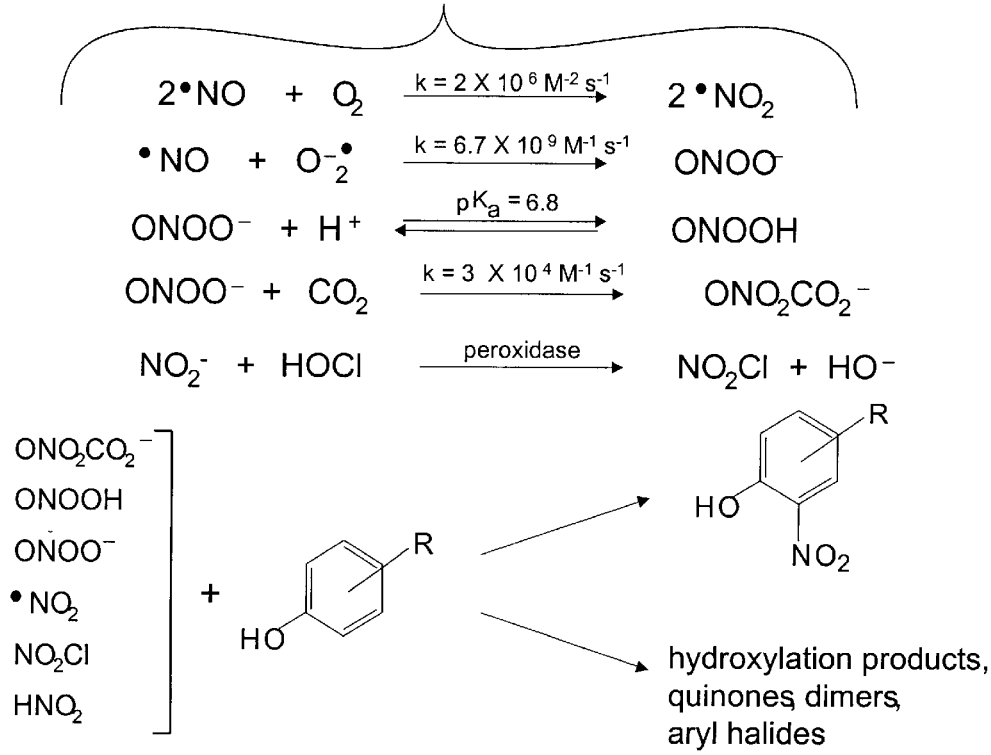
FIG. 2 shows pathways for generation of nitrating agents and their subsequent reaction with phenolic substrates such as tyrosine or γ-tocopherol.

The present application demonstrates the superiority of desmethyl tocopherols, exemplified by gamma tocopherol, as protectors against nitrative damage to biological systems. The results described here are novel in several respects. Particularly, the results demonstrate that gamma tocopherol (γ-tocopherol or γT) is superior to alpha tocopherol (α-tocopherol or αT) (i.e., vitamin E, a fully alkylated tocopherol) in systems where nitrative stress is a relevant phenomenon. The invention of this utility for γ-tocopherol (and other desmethyl tocopherols) is not obvious to ordinarily skilled practitioners of the art of antioxidant therapy. This contention is demonstrated by the fact that only α-tocopherol is currently being studied as a clinically relevant antioxidant in the treatment of cardiovascular or neurodegenerative disease (15). In clinical studies performed to date, α-tocopherol has failed to provide a consistent beneficial effect on outcome parameters (32–33, 25–38). In point off act, oral supplementation of humans with α-tocopherol actually depletes the human body of γ-tocopherol (reference 3 and the present inventors' observations).

γ-Tocopherol and other desmethyl tocopherols are present in natural foods (particularly soy and wheat) in small amounts and are generally regarded as safe for human subjects. The biological activity of desmethyl tocopherols is associated with the chromanol head group of the molecule (indicated by arabic numbers in the structure above). This is to distinguish the tocopherols from tocotrienols, which inhibit cholesterol biosynthesis but whose activity is resident in the unsaturated lipid tail of the tocotrienol molecule. Gamma tocopherol (and other desmethyl tocopherols) may be chemically synthesized or isolated from natural products.

In practice, the γ-tocopherol (or other desmethyl tocopherols) would be formulated in a manner allowing safe delivery of effective doses to humans. The γ-tocopherol (or other desmethyl tocopherols) can be absorbed orally by mammals and could be used by oral administration. The γ-tocopherol (or other desmethyl tocopherols) could be administered topically to inflamed skin or gum/mouth or other mucosal tissue as a cream or gel, or could be inhaled as an aerosol. The relative stability and lipophilicity of γ-tocopherol (and other desmethyl tocopherols) make these compounds amenable to delivery in numerous possible formulations. Derivatives of γ-tocopherol (or other desmethyl tocopherols) which retain the structure of a phenolic ring lacking a H atom near the —OH group would also be usefull as a protectant against nitrative stress in neurodegenerative conditions; intraperitioneal or intravascular administration in appropriate media may also be used when desired.

As a cardioprotectant or neuroproctectant, oral γ-tocopherol supplements could be taken at a dose of 100–4000 mg/day by individuals suffering from or at risk for cardiovascular or neurological diseases. The γ-tocopherol supplements would consist of γ-tocopherol alone or as a predominant component mixed with other tocopherols, medications or nutritive supplements. As a component of topical products or for intravenous administration, γ-tocopherol could be used alone or in combination with α-ketoglutarate and/or other tocopherols. In these applications, effective in vivo concentrations would likely be from about 1 μM to about 10 mM, more preferably from about 1 mM to about 10 mM.

After consideration of the data described below, these and other advantages and objects of the invention will be apparent to those skilled in the art. The following examples are intended for illustrative purpose only and are not to be construed as limiting the invention in sphere or scope.

EXAMPLE 1

Figure 3:
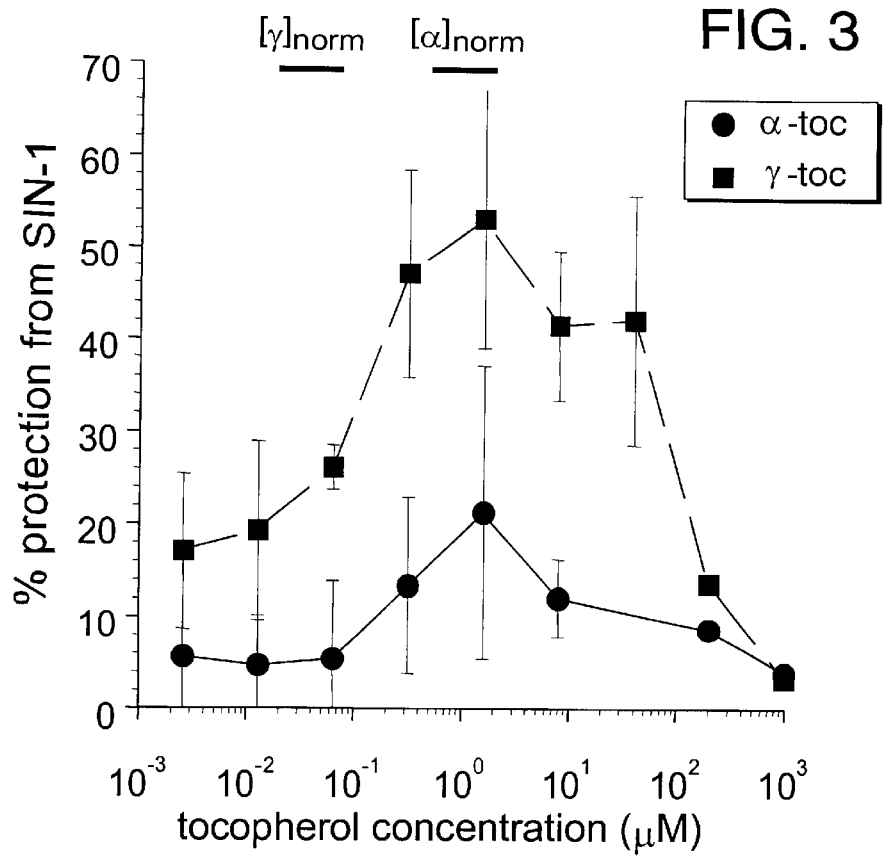
FIG. 3 is a graph showing rat brain mitochondria exposed to 0.4 mM SIN-1 for 1 H after addition of tocopherol. (●)α-tocopherol; (■)γ-tocopherol. The scale bars labeled $[\alpha]_{norm}$ and $[Y]_{norm}$ indicate the normal endogenous quantities of α-tocopherol and γ-tocopherol, respectively, in human brain.

Demonstration of αKGDH Protection Against Nitrative Stress by Gamma Tocopherol

αKGDH is a rate-limiting enzyme of mitochondrial energy production which is diminished in conditions of vascular ischemia (53–58); augmentation of the enzyme with α-ketoglutarate has been found beneficial and α-ketoglutarate is now included as a component in cardioplegia fluid to improve recovery after heart surgery (59). We undertook to determine whether γT protects αKGDH against nitrative stress in vitro. Mitochondria were isolated from adult rat brain then sonicated briefly in the presence of either αT or γT, or an ethanol vehicle. Mitochondria were then exposed to SIN-1, which generates NO and superoxide simultaneously at a known rate (7). Combination of NO and superoxide yields ONOO⁻. in situ (discussed above). FIG. 3 illustrates the protection of αKGDH by αT and γT present during exposure to the peroxynitrite (RNS)-generating compound SIN-1. A 400 μM concentration of SIN-1 was sufficient to diminish αKGDH activity by approximately 50% in one hour. Under these conditions of nitrative stress, the αKGDH activity varied in a biphasic manner with respect to tocopherol concentration. At higher tocopherol concentrations, the reaction medium became grossly turbid so that the apparent loss of enzyme activity might reflect a nonspecific physical consequence of the extreme lipid content. At all concentrations tested, γT was more protective than αT when tested in side-by-side comparisons. Maximal protection was observed at 1 μM tocopherol in the case of both αT and γT (FIG. 3). The maximal protection by γT was approximately 2.5 times greater than the maximal protection afforded by αT. At concentrations near 100 nM, γT was approximately 5 times more protective than the corresponding concentration of αT. Moreover, 50–100 nM of γT offered as much protection as 1–10 μM αT. Thus, γT may be as important (or more important) an antioxidant as αT during nitrative stress, despite the lower intrinsic concentration of γT in most mammalian tissue.

EXAMPLE 2

Figure 4:
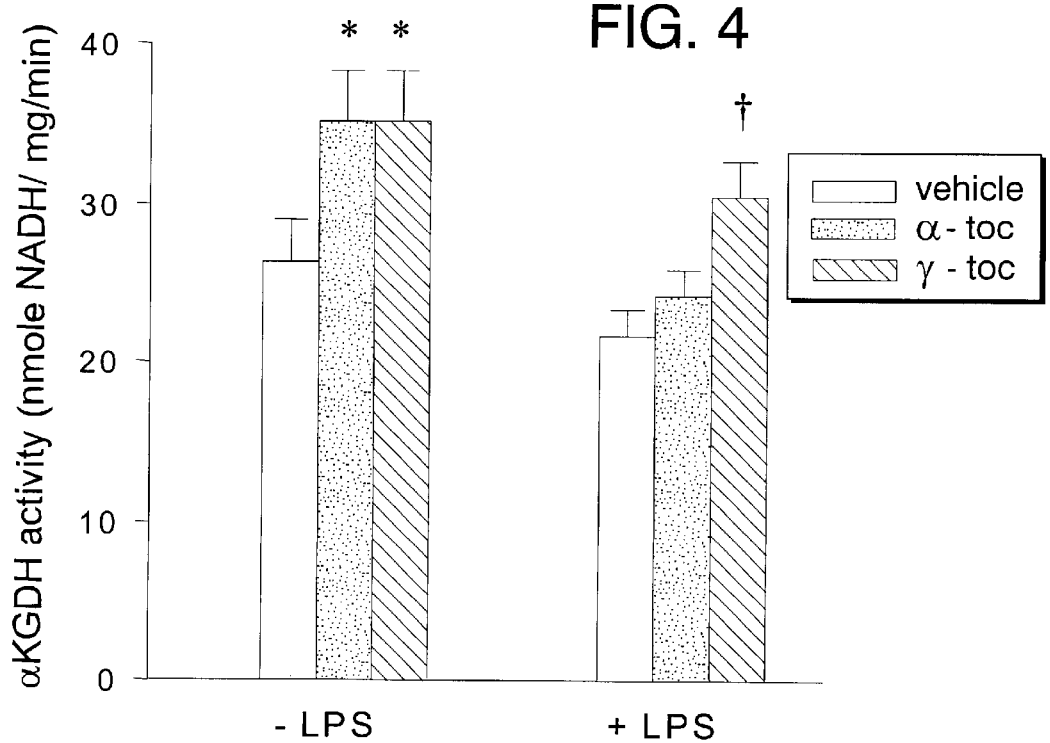
FIG. 4 is a graph showing tocopherol effects on αKGDH in vivo. Rats were injected with 15 mg of tocopherol over the first 1 month of life; specific groups were then challenged with a septic dose of LPS and heart αKGDH activity was assayed 24 H later. *$p<0.1$ relative to vehicle; †$p<0.05$ relative to vehicle. N=5/group.

Demonstration of αKGDH Protection Against Nitrative Stress In Vivo by Gamma Tocopherol Rat pups were injected intraperitoneally (I.P.) with αT or γT in an olive oil vehicle every other day for 30 days beginning 2 days after birth; control animals received vehicle only. Olive oil was chosen as a vehicle because of the low tocopherol content in this particular vegetable oil. A total of 15 mg tocopherol was delivered to each animal over the 30 day period; animal weight at the end of the period was approximately 90 g for all three groups. One half of each animal group was injected with a septic dose of LPS (2.5 mg/kg, I.P). After 24 H, animals were killed and organs collected. αKGDH was assayed in heart tissue and tocopherols were measured by HPLC-ECD/PDA. The supplementation paradigm was sufficient to approximately double the heart tissue level of both αT and γT [αT concentration= 23±12 ng/mg protein in controls vs. 48±13 ng/mg in αT supplemented animals (N=5); γT concentration=1.8±0.4 ng/mg protein in controls vs. 3.9±0.7 ng/mg in γT supplemented animals (N=5)]. Similar changes were noted in plasma tocopherol concentrations (not shown). The effect of tocopherol supplementation on cardiac αKGDH activity is illustrated in FIG. 4. Both αT and γT supplementation increased mean αKGDH activity by 40% in animals not subjected to LPS stress. This increase was significant at the 90% confidence level (p<0.1 by Student's t-test). In LPS-treated animals, αKGDH activity decreased by 20–40% in all groups. Notably, the γT supplemented animals maintained the highest heart αKGDH activity among the several groups after LPS challenge (FIG. 4). These data indicate that γT supplementation is at least as effective and probably more effective at maintaining mitochondrial homeostasis under a condition where nitrative stress is known to be relevant.

EXAMPLE 3

Demonstration of Endothelial Cell Protection by γ-Tocopherol

Figure 5:
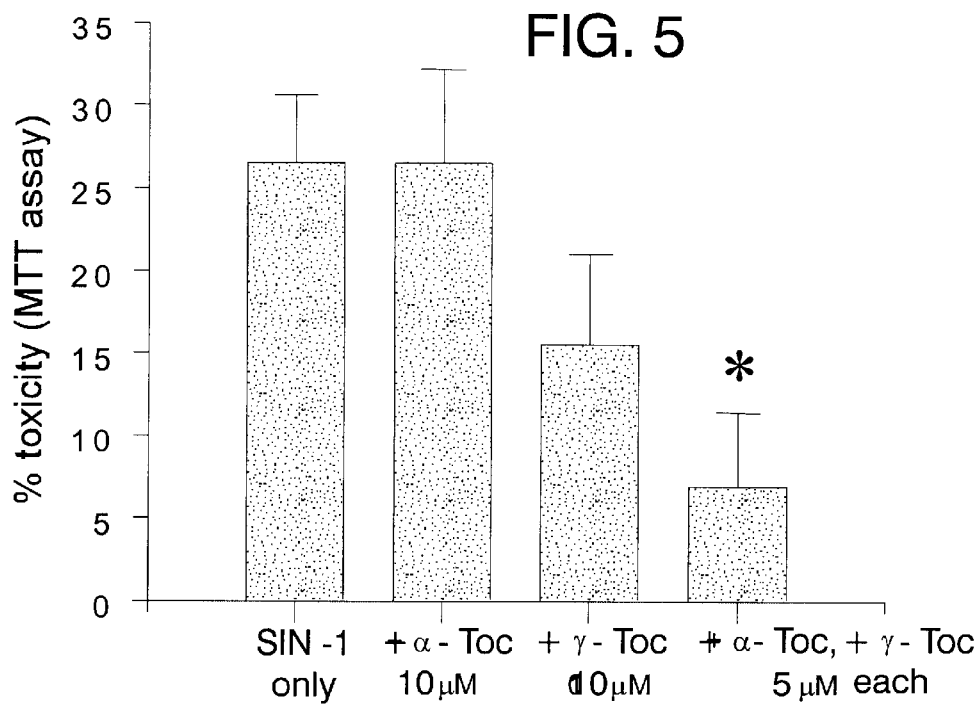
FIG. 5 is a graph showing influence of α-toc and γ-toc on viability of ECV034 endothelial cells exposed to SIN-1 as assessed by ability of viable cells to reduce the tetrazolium dye MTT>N=5 experiments. *$P<0.05$ relative to cells which had received SIN-1 only.

Cultured ECV304 human endothelial cells were exposed to SIN-1 in the presence of 10 μM α-T, 10 μM γ-T or 5 μM of each (FIG. 5). Tocopherols were incubated with the cells for 19 hours prior to addition of SIN-1. Viability was assayed 24 hours later using a standard tetrazolium (MTT) reduction assay. These cells proved very resistant to damage by SIN-1; however, a 5 mM initial concentration of SIN-1 produced approximately 26% toxicity within 24 hours (N=5; FIG. 5). While α-T had no apparent effect on SIN-1 toxicity, γ-T promoted viability somewhat and the combination of γ-T with α-T (1:1 molar ratio) completely prevented SIN-1 toxicity (FIG. 5). The data suggest that γ-T may protect cells in a way that α-T does not.

EXAMPLE 4

γT Scavenges Reactive Nitrogen Species in Smokers and Hypertensive Individuals

Smoking is recognized as a major contributing factor to heart disease and γ-T reportedly decreases more than α-T in smokers. Hypertension is also a strong risk factor for heart disease. We have begun collection of data from "normal" subjects who do not currently have CAD, including smokers and nonsmokers, and hypertensive subjects. 11 of 54 volunteers from the Oklahoma City Veteran's Administration Hospital and the Oklahoma Medical Research Foundation indicated a current smoking habit. Seven subjects indicated a chronic hypertensive condition. As outlined in Table I, γ-tocopherol tended to decrease in hypertensive subjects while nitration products tended to increase in both smokers and hypertensive subjects. This was the trend regardless of whether the tocopherol concentrations were normalized to plasma triglycerides (Table I).

TABLE I

Preliminary statistical data regarding plasma concentrations of α-tocopherol, γ-tocopherol and 5-NO₂ γ-tocopherol in a population of random volunteers from Oklahoma City.

|  | population mean ± SEM N = 54 | smokers mean ± SEM N = 7 | hypertensives mean ± SEM N = 7 |
|---|---|---|---|
| α-tocopherol |  |  |  |
| μg/mL plasma | 18.3 ± 2.6 | 24.9 ± 9.2 | 23.1 ± 12.2 |
| μg/mg triglyceride | 34.2 ± 14.2 | 21.5 ± 4.5 | 21.9 ± 5.9 |
| γ-tocopherol |  |  |  |
| μg/mL plasma | 0.713 ± 0.067 | 0.680 ± 0.153 | 0.463 ± 0.165 |
| μg/mg triglyceride | 0.813 ± 0.088 | 0.810 ± 0.213 | 0.606 ± 0.153 |
| γ-toc/α-toc × 100 | 6.78 ± 1.13 | 5.54 ± 1.26 | 4.29 ± 1.40 |
| 5-NO₂-γ-tocopherol |  |  |  |
| ng/mL plasma | 11.3 ± 1.6 | 20.0 ± 3.3 | 20.0 ± 3.7 |
| ng/mg triglyceride | 14.0 ± 2.5 | 23.5 ± 7.2 | 34.9 ± 10.9 |
| 5-NO₂-γ-toc/γ-toc × 1000 | 3.49 ± 0.74 | 5.47 ± 1.96 | 8.20 ± 2.21 |

EXAMPLE 5

γT Scavenges Reactive Nitrogen Species During Thrombosis in an Animal Model

Figure 6:
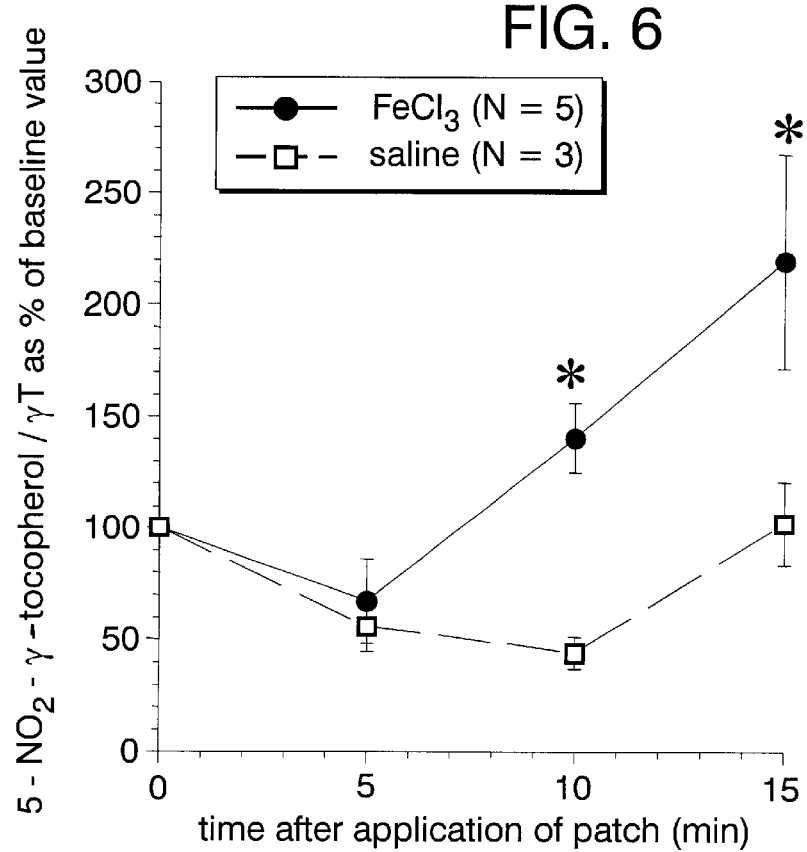
FIG. 6 is a graph showing nitration of plasma γ-tocopherol in vivo during $FeCl_3$-induced thrombosis in the rat. *Significant increase above baseline values (i.e., before initiation of thrombosis; $p<0.05$, N=5).

As discussed above, γT has been found much more effective than αT in the inhibition of thrombosis in a rat model (Saldeen et al. reference 9). Consequently, we set forth to determine whether 5-$NO_2$-γ-toc might be formed during thrombosis in vivo. In a first experiment, the Saldeen model was used to induce occlusive thrombosis by application of an $FeCl_3$-laden patch to the descending aorta of anesthetized rats. 0.2 mL samples of blood were withdrawn into a 2 mM EDTA saline solution by heart puncture at various time points after application of the $FeCl_3$-laden patch. Control experiments were conducted using a saline-soaked patch, which does not induce thrombosis. Plasma was isolated by centrifugation of the blood and was analyzed by HPLC-ECD. As illustrated in FIG. 6, 5-$NO_2$-γ-tocopherol was formed within minutes after initiation of thrombosis and increased steadily until the animal died (approximately 20 min. after initiation of thrombosis). Plasma nitrite concentrations were not statistically altered in this model of thrombogenesis. The increase in 5-$NO_2$-γ-tocopherol/γ-tocopherol was due both to a decrease in γ-tocopherol and an increase in 5-$NO_2$-γ-tocopherol; α-tocopherol was not substantially affected by $FeCl_3$-induced thrombosis (data not illustrated).

EXAMPLE 6

γ-Tocopherol Inhibits Platelet Aggregation

γT inhibits platelet aggregation in vitro and in vivo, apparently through antagonism of protein kinase C (PKC) (60–63). Concentrations of αT necessary to inhibit aggregation in vitro are on the order of 500 $\mu$M (60–63), or approximately 10-fold higher than achieved in vivo. The concentration difference between in vitro and in vivo efficacy has been rationalized on the basis of incomplete tocopherol incorporation into membranes during in vitro incubation (63). Nonetheless, subjects supplemented with oral αT have diminished platelet aggregation (63). We therefore sought to investigate the ability of γ-tocopherol to inhibit platelet aggregation. PRP was obtained from two volunteers. Platelets were stimulated to aggregate with ADP, thrombin receptor activating peptide (TRAP) or the PKC agonist phorbol myristyl acetate (PMA) and aggregation was measured using a 4-channel clinical aggregometer. Specific platelet samples were preincubated with vehicle, αT, γT or 5-$NO_2$-γ-tocopherol for 1 H prior to stimulation. Tocopherol concentrations were set at 10-fold excess to average PRP levels based on the precedent of previous in vitro aggregation experiments that used αT as an inhibitor (60–63). As shown in Table II, γT was similarly efficacious to αT when tested for ability to inhibit PKC-linked platelet aggregation (e.g., when TRAP or PMA was used as the agonist). This data suggests that γT has an activity similar to αT with respect to antagonism of PKC-dependent platelet aggregation and corresponding thrombogenic events, while other data (see above) indicates specifically enhanced RNS scavenging ability inherent to the γT structure.

TABLE II effect of tocopherols on platelet aggregation in vitro.
% maximum = 100% × (aggregability with added tocopherol/aggregability without added tocopherol).

| | | Platelet Aggregation (% maximum) | | |
|---|---|---|---|---|
| | | ADP 20 $\mu$M | TRAP 20 $\mu$M | PMA 200 nM |
| Subject 1 | vehicle (ethanol) | 100 | 100 | 100 |
| | 500 $\mu$M α-tocopherol | 85 | 44 | 74 |
| | 50 $\mu$M γ-tocopherol | 117 | 73 | 57 |

TABLE II-continued effect of tocopherols on platelet aggregation in vitro.
% maximum = 100% × (aggregability with added tocopherol/aggregability without added tocopherol).

| | | Platelet Aggregation (% maximum) | | |
|---|---|---|---|---|
| | | ADP 20 $\mu$M | TRAP 20 $\mu$M | PMA 200 nM |
| Subject 2 | vehicle (ethanol) | 100 | 100 | 100 |
| | 500 $\mu$M α-tocopherol | 72 | 75 | 34 |
| | 50 $\mu$M γ-tocopherol | 90 | 88 | 29 |

REFERENCES

The following references are incorporated in pertinent part by reference herein for the reasons cited.

1. Bieri, J. G., Evarts, R. P. Gamma tocopherol: Metabolism, biological activity and significance in human vitamin E nutrition. *J. Clin. Nutr.* 27: 980–985; 1974.

2. Lehmann, J.; Martin, H. L.; Lashley, E. L.; Marshall, M. W.; Judd, J. T. Vitamin E in foods from high and low linoleic acid diets. *J. Am. Diet. Assoc.* 86, 1208–1216; 1986.

3. Handelman, G. J.; Machlin, L. M.; Fitch, K.; Weiter, J. J.; Dratz, E. A. Oral α-tocopherol supplements decrease plasma γ-tocopherol levels in humans. *J. Nutr.* 115: 807–813; 1985.

4. Raber, M. G.; Burton, G. W.; Hughes, L.; Ingold, K. U.; Hidaka, H.; Malloy, M.; Kane, J.; Hyams, J.; Kayden, H. J. Discrimination between forms of vitamin E by humans with and without genetic abnormalities of lipoprotein metabolism. *J. Lipid Res.* 33, 1171–1182; 1992.

5. Cooney, R. V.; Franke, A. A.; Harwood, P. J.; Hatch-Pigott, V.; Custer, L. J.; Mordan, L. J. γ-Tocopherol detoxification of nitrogen dioxide: Superiority to α-tocopherol. *Proc. Natl. Acad. Sci. USA.* 90: 1771–1775, 1993.

6. Christen, S.; Woodall, A. A.; Shigenaga, M. K.; Southwell-Keely, P. T.; Duncan, M. W.; Ames, B. N. γ-Tocopherol traps mutagenic electrophiles such as NOx and complements α-tocopherol: Physiological implications. *Proc. Natl. Acad. Sci. USA* 94: 3217–3222; 1997.

7. Goss, S. P. A.; Hogg, N.; Kalyanaraman, B. The effect of α-tocopherol on the nitration of γ-tocopherol by peroxynitrite. *Arch. Biochem. Biophys.* 363: 333–340; 1999.

8. Dillard, C. J.; Gavino, V. C.; Tappel, A. L. Relative antioxidant effectiveness of α-tocopherol and γ-tocopherol in iron-loaded rats. *J. Nutr.* 113: 2266–2273; 1983.

9. Saldeen, T.; Li, D.; Mehta, J. L. Differential effects of alpha- and gamma-tocopherol on low-density lipoprotein oxidation, superoxide activity, platelet aggregation and arterial thrombogenesis. *J. Am. Coll. Cardiol.* 34: 1208–1215; 1999.

10. Tran, K.; Chan, A. C. Comparative uptake of alpha- and gamma-tocopherol by human endothelial cells. *Lipids* 27: 38–41; 1992.

11. Brown, M. S.; Goldstein, J. L. A receptor-mediated pathway for cholesterol homeostasis. *Science* 232: 34–37; 1986.

12. Goldstein, J. L.; How, Y. K.; Basu, S. K.; Brown, M. S. Binding site on macrophages that mediates uptake and degradation of acetylated low density lipoprotein, producing massive cholesterol deposition. *Proc. Natl. Acad. Sci. USA* 76: 333–337; 1979.

13. Palinski, W.; Rosenfeld, M. E.; Yla-Herttuala, S.; Gurtner, G. C.; Socher, S. S.; Butler, S. W.; Parthasarathy, S.; Carew, T. E.; Steinberg, D.; Witztum, J. L. Low density lipoprotein undergoes oxidative modification in vivo. *Proc. Natl. Acad. Sci. USA* 86: 1372–1376; 1989.

14. Quinn, M. T.; Parthasarathy, S.; Fong, L. G.; Steinberg, D. Oxidatively modified low density lipoproteins: A potential role in recruitment and retention of monocyte/macrophages during atherogenesis. *Proc. Natl. Acad. Sci. USA* 84: 2995–2998; 1987.

15. Witztum, J.; Steinberg, D. Role of low density lipoprotein in atherogenesis. *J. Clin. Invest.* 88: 1785–1792; 1991.

16. Esterbauer, H.; Gebicki, J.; Puhl, H.; Jurgens, G. The role of lipid peroxidation and antioxidants in modification of LDL. *Free Rad. Biol Med.* 13: 341–390; 1992.

17. Steinbrecher, U. P.; Lougheed, M. Scavenger receptor-independent stimulation of cholesterol esterification in macrophages by low density lipoprotein extracted from human aortic intima. *Arterioscler. Thromb.* 12: 608–625; 1992.

18. Jessup, W.; Rankin, S. M.; De Whalley, C. V.; Hoult, J. R. S.; Scott, J.; Leake, D. S. α-Tocopherol consumption during low-density lipoprotein oxidation. *Biochem. J.* 265: 399–405; 1990.

19. Suarna, C.; Dean, R. T.; May, J.; Stocker, R. Human artherosclerotic plaque contains both oxidized lipids and relatively large amounts of alpha tocopherol and ascorbate. *Arteioscler. Thromb. Vasc. Biol.* 15: 1616–1624; 1995.

20. Diaz, M. N.; Frei, B.; Vita, J. A.; Keaney, J. F. Jr. Antioxidants and atherosclerotic heart disease. *New Eng. J. Med.* 337: 408–416; 1997.

21. Baker, C. S.; Hall, R. J.; Evans, T. J.; Pomerance, A.; Maclouf, J.; Creminon, C.; Yacoub, M. H.; Polak, J. M. Cyclooxygenase-2 is widely expressed in atherosclerotic lesions affecting native and transplanted human arteries and colocalizes with inducible nitric oxide synthase and nitrotyrosine particularly in macrophages. *Arterioscler. Thromb. Vasc. Biol.* 19: 646–655; 1999.

22. Luoma, J. S.; Stralin, P.; Marklund, S. L.; Hiltunen, T. P.; Sarkioja, T.; Yla-Herttuala, S. Expression of extracellular SOD and iNOS in macrophages and smooth muscle cells in human and rabbit atherosclerotic lesions: Colocalization with epitopes characteristic of oxidized LDL and peroxynitrite-modified proteins. *Arterioscler. Thromb. Vasc. Biol.* 18: 157–167; 1998.

23. Buttery, L. D.; Springall, D. R.; Chester, A. H.; Evans, T. J.; Standfield, E. N.; Parums, D. V.; Yacoub, M. H.; Polak, J. M. Inducible nitric oxide synthase is present within human atherosclerotic lesions and promotes the formation and activity of peroxynitrite. *Lab Invest.* 75: 77–85; 1996.

24. Luoma, J. S.; Yla-Herttuala, S. Expression of inducible nitric oxide synthase in macrophages and smooth muscle cells in various types of human atherosclerotic lesions. *Virchows Arch* 434: 561–568; 1999.

25. Behr, D.; Rupin, A.; Fabiani, J. N.; Verbeuren, T. J. Distribution and prevalence of inducible nitric oxide synthase in atherosclerotic vessels of long-term cholesterol-fed rabbits. *Atherosclerosis* 142: 335–344; 1999.

26. Leeuwenburgh, C.; Hardy, M. M.; Hazen, S. L.; Wagner, P.; Oh-ish, S.; Steinbrecher, U. P.; Heinecke, J. W. Reactive nitrogen intermediates promote low-density lipoprotein oxidation in human atherosclerotic intima. *J. Biol. Chem.* 17: 1433–1436; 1997.

27. Moriel, P.; Abdalla, D. S. Nitrotyrosine bound to beta-VLDL apoproteins: A biomarker of peroxynitrite formation in experimental atherosclerosis. *Biochem. Biophys. Res. Commun.* 232: 332–335; 1997.

28. Spencer, A. P.; Carson, D. S.; Crouch, M. A. *Arch. Intern. Med.* 159:1313–1320; 1999.

29. Gey, K. F.; Puska, P.; Moser, U. K. Inverse correlation between plasma vitamin E and mortality from ischemic heart disease in cross-cultural epidemiology. *Am. J. Clin. Nutr.* 53 (suppl. 1): 326S-334S; 1991.

30. Stampfer, M. J.; Hennekens, C. H.; Manson, J. E.; Colditz, G. A.; Rosner, B.; Willett, W. C. Vitamin E consumption and the risk of coronary artery disease in women. *N. Engl. J. Med.* 328; 1444–1449; 1993.

31. Rimnm, E. B.; Stampfer, M. J.; Ascherio, A.; Giovannucci, E.; Colditz, G. A.; Willett, W. C. Vitamin E consumption and risk of coronary heart disease in men. *N. Engl. J. Med.* 328: 1450–1456; 1993.

32. Stephens, N. G.; Parsons, A.; Schofield, P. M.; Kelly, F.; Cheeseman, K.; Mitchinson, M. J. Randomised controlled trial of vitamin E in patients with coronary disease: Cambridge Heart Antioxidant Study (CHAOS) *Lancet* 347: 781–786; 1996.

33. Rapola, J. M.; Virtamo, J.; Ripatti, S.; Huttumen, J. K.; Albanes, D.; Taylor, P. R.; Heinonen O. P. Randomised trial of alpha tocopherol and beta carotene supplements on incidence of major coronary events in men with previous myocardial infarction. *Lancet* 349: 1715–1720; 1997.

34. Subcommittee on the Tenth Edition of the RDAS, Food and Nutrition board, Comission on Life Sciences, National Research Council. Recommended Dietary Allowances. $10^{th}$ ed. Washington, DC: National Academy Press; 1989.

35. The alpha-tocopherol beta carotene cancer prevention study group. The effect of vitamin E and beta carotene on the incidence of long cancer and other cancers in male smokers. *New Engl. J. Med.* 330: 1029–1035; 1994.

36. Kushi, L. H.; Folsom, A. R.; Prineas, R. J.; Mink, P. J.; Wu, Y.; Bostick, R. M. Dietary antioxidant vitamins and death from coronary heart disease in postmenopausal women. *N. Engl. J. Med.* 328: 1156–1162; 1996.

37. Stocker, R. The ambivalence of vitamin E in atherogenesis. *Trends Biol. Sci.* 24: 219–223; 1999.

38. The heart outcomes prevention evaluation study investigators. Vitamin E supplementation and cardiovascular events in high-risk patients. *New Engl. J. Med.* 342: 154–160; 2000.

39. Traber, M. G.; Burton, G. W.; Hughes, L.; Ingold, K. U.; Hidaka, H.; Malloy, M.; Kane, J.; Hyams, J.; Kayden, H. J. Discrimination between forms of vitamin E by humans with and without genetic abnormalities of lipoprotein metabolism. *J. Lipid Res.* 33, 1171–1182; 1992.

40. Lehmann, J.; Martin, H. L.; Lashley, E. L.; Marshall, M. W.; Judd, J. T. Vitamin E in foods from high and low linoleic acid diets. *J. Am. Diet. Assoc.* 86, 1208–1216; 1986.

41. Handehnan, G. J.; Machlin, L. M.; Fitch, K.; Weiter, J. J.; Dratz, E. A. Oral α-tocopherol supplements decrease plasma γ-tocopherol levels in humans. *J. Nutr.* 115: 807–813; 1985.

42. Saldeen, T.; Li, D.; Mehta, J. L. Differential effects of alpha- and gamma-tocopherol on low-density lipoprotein oxidation, superoxide activity, platelet aggregation and arterial thrombogenesis. *J. Am. Coll. Cardiol.* 34:1208–1215; 1999.

43. Kontush, A.; Spranger, T.; Reich, A.; Baum, K.; Beisiegel, U. Lipophilic antioxidants in blood plasma as markers of atherosclerosis: The role of α-carotene and γ-tocopherol. *Atherosclerosis* 144: 117–122; 1999.

44. Ohrvall, M.; Sundlof, G.; Vessby, B. Ganuna, but not alpha, tocopherol levels in serum are reduced in coronary heart disease patients. *J. Int. Med.* 239: 111–117; 1996.

45. Brown, A. J. Acute effects of smoking cessation on antioxidant status. *J. Nutr. Biochem.* 7: 29–39; 1996.

46. Cooney, G. J.; Taegtmeyer, H.; Newsholme, E. A. Tricarboxylic acid cycle flux and enzyme activities in the isolated working rat heart. *Biochem. J.* 200: 701–703; 1981.

47. Lucas, D. T.; Szweda, L. I. Declines in mitochondrial respiration during cardiac reperfusion: Age-dependent inactivation of alpha ketoglutarate dehydrogenase. *Proc. Natl. Acad. Sci. USA* 96: 6689–6693.

48. Brown, J. P.; Perham, R. N. Selective inactivation of the transacylase components of the 2-oxoacid dehydrogenase multienzyme complexes of *Escherichia coli. Biochem. J.* 155:419–427; 1976.

49. Andersson, U.; Leighton, B.; Young, M. E.; Blomstrand, E.; Newshohne, E. A. Inactivation of aconitase and oxoglutarate dehydrogenase in skeletal muscle in vitro by superoxide anions and/or nitric oxide. *Biochem. Biophys. Res. Commun.* 249: 512–516.

50. Park, L. C.; Zhang, H.; Sheu, K. F.; Calingasan, N. Y.; Kristal, B. S.; Lindsay, J. G.; Gibson, G. E. Metabolic impairment induces oxidative stress, compromises inflammatory responses, and inactivates a key mitochondrial enzyme in microglia. *J. Neurochem.* 72: 1948–1958; 1999.

51. Kjellman, U.; Bjork, K.; Ekroth, R.; Karlsson, H.; Jagenburg, R.; Nilsson, F.; Svensson, G.; Wernerman, J. Alpha-ketoglutarate for myocardial protection in heart surgery. *Lancet* 345: 552–553; 1995.

52. Kjellman, U. W.; Bjork, K.; Ekroth, R.; Karlsson, H.; Jagenburg, R.; Nilsson, F. N.; Svensson, G.; Wemerman, J. Addition of alpha-ketoglutarate to blood cardioplegia improves cardioprotection. *Ann. Thorac. Surg.* 63: 1625–1633; 1997.

53. Freedman, J. E.; Farhat, J. H.; Loscalzo, J.; Keaney, J. F. Jr. α-Tocopherol inhibits aggregation of human platelets by a protein kinase C-dependent mechanism. *Circulation* 94: 2434–2440; 1996.

54. Keaney, J. F. Jr.; Simon, D. I.; Freedman, J. Vitamin E and vascular homeostasis: Implications for atherosclerosis. *FASEB J.* 13: 965–976; 1999.

55. Pignatelli, P.; Pulceinelli, F. M.; Lenti, L.; Gazzaniga, P. P.; Violi, F. Hydrogen peroxide is involved in collagen-induced platelet activation. *Blood* 91: 484–490; 1998.

56. Pignatell, P.; Pulcinelli, F. M.; Leni, L.; Gazzaniga, P. P.; Violi, F. Vitamin E inhibits collagen-induced platelet activation by blunting hydrogen peroxide. *Arterioscler. Thromb. Vasc. Biol.* 19: 2542–2547; 1999.

What is claimed is:

1. A method of delaying or preventing cardiovascular disease which comprises the administration of an effective amount of at least one desmethyl tocopherol.

2. A method of delaying or preventing symptoms and consequences of cardiovascular disease which comprises the administration of an effective amount of gamma tocopherol.

3. A method of inhibiting cardiovascular damage resulting from thrombosis which comprises administration of an effective amount of at least one desmethyl tocopherol.

4. The method of claim 1, or 2 wherein said cardiovascular disease is atherosclerosis, coronary artery disease or ischemic injury.

5. A method of inhibiting cardiovascular tissue damage resulting from exposure to nitrative stress which consists essentially of the administration of an effective amount of gamma tocopherol.

6. The method of claim 1, or 3 wherein said desmethyl tocopherol is in pure form or in mixtures or formulations with drugs or other antioxidants.

7. A method of preserving αKGDH activity in cardiovascular tissue exposed to nitrative stress which consists essentially of the administration of a safe and effective amount of gamma tocopherol.

8. The method of claim 7 wherein said gamma tocopherol is administered orally, intravenously or in cardioplegia fluid.

9. A method of preserving mitochondrial function in cardiovascular tissue which comprises administration of an effective amount of at least one desmethyl tocopherol.

10. The method of claim 9 wherein said desmethyl tocopherol is administered orally, intravenously or in cardioplegia fluid.

11. The method of any one claim 1, 2, or 3 wherein the tocopherol is used as a mixture of isomers.

12. The method of claim 1, 2, or 3 wherein the tocopherol is isolated from natural products.

13. The method of claim 1, 2, or 3 wherein the tocopherol is synthetically prepared.

14. The method of claim 1, 2, or 3 wherein the tocopherol is administered as a prodrug.

15. The method of claim 1, 2, or 3 wherein the tocopherol is administered as a water-soluble ester.

16. The method of claim 1, 2, or 3 wherein the tocopherol is orally administered at a daily dose of from about 100 to about 400 mg.

* * * * *